United States Patent [19]

Kim

[11] Patent Number: 4,556,516

[45] Date of Patent: Dec. 3, 1985

[54] PROCESS FOR THE PREPARATION OF ACYLUREIDO PENICILLIN DERIVATIVES

[75] Inventor: Don K. Kim, Seoul, Rep. of Korea

[73] Assignee: Boryung Pharmaceutical Co., Ltd., Seoul, Rep. of Korea

[21] Appl. No.: 577,755

[22] Filed: Feb. 7, 1984

[30] Foreign Application Priority Data

Dec. 19, 1983 [KR] Rep. of Korea .................. 5991/1983

[51] Int. Cl.[4] .......................................... C07D 499/70
[52] U.S. Cl. ........................... 260/239.1; 260/245.2 R; 548/351; 548/320
[58] Field of Search .................. 260/239.1; 544/25, 27, 544/28

[56] References Cited

U.S. PATENT DOCUMENTS 3,933,795  1/1976  Disselnkotter et al. ......... 260/239.1
4,223,037  9/1980  Preiss et al. ...................... 260/239.1
4,235,774  11/1980  Preiss et al. ...................... 260/239.1

FOREIGN PATENT DOCUMENTS 767648  11/1981  Belgium .

*Primary Examiner*—Natalie Trousof
*Assistant Examiner*—Vera C. Clarke
*Attorney, Agent, or Firm*—Cushman, Darby & Cushman

[57] ABSTRACT

A process for the preparation of acylureido penicillin derivatives is disclosed. In particular this invention concerns an economical process for the preparation with high yield of penicillin derivatives of the formula

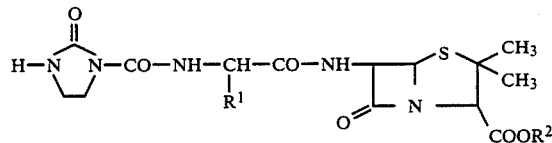

where $R^1$ represents phenyl or hydroxyphenyl and $R^2$ a member selected from the group consisting of hydrogen, a protecting group, sodium, potassium and calcium. The compounds are useful as anti-bacterial agents for human and animals.

2 Claims, No Drawings

PROCESS FOR THE PREPARATION OF ACYLUREIDO PENICILLIN DERIVATIVES

TECHNICAL FIELD

This invention relates to a novel process for the preparation of acylureido penicillin derivatives which are useful as anti-bacterial agents for human and animals and, more particularly, to an economical process for the preparation with high yield of penicillin derivatives having the following formula:

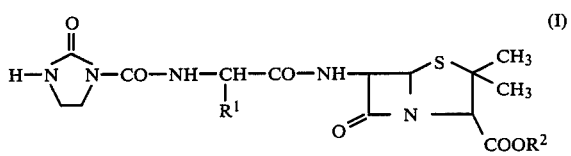

wherein
R¹ is phenyl or hydroxyphenyl; and
R² is a member selected from the group consisting of hydrogen, protecting group, sodium, potassium and calcium.

BACKGROUND ART

Penicillin derivatives which have acylureido group in α-position of 6-acylamide side chain are described in Belgium Pat. No. 767,648; German Pat. Nos. 2,025,415 and 2,104,579; Japan Pat. No. 7,107,335; Republic of South Africa Pat. No. 7,103,274; and U.S. Pat. No. 3,933,795.

Conventional processes were usually concerned to methods for preparing acylureido penicillin derivatives in the course which 1-chlorocarbonyl-imidazolidine-2-one as intermediate is synthesized with phosgene gas that have potent toxicity, and then this intermediate has reacted with penicillin derivatives to yield object compounds. U.S. Pat. No. 3,933,795 have reported a process for the preparation of ureidoacetamido-penicillin by the reaction of 6-amino-penicillanic acid and carbonylchloride of the formula:

$$A-CO-NH-CH-COCl.$$
$$\qquad\qquad\qquad |$$
$$\qquad\qquad\qquad B$$

But no process using ethylenediisocyanate as starting material has as yet been reported.

DISCLOSURE OF THE INVENTION

The present invention provides a novel process for the preparation of the above penicillin derivatives with more ease and high yield according to the way different from reported patents, and also provides a particularly economical process for the preparation of acylureido penicillin derivatives which have potent activity for gram-positive and gram-negative bacteria through use of ethylenediisocyanate as starting material.

Two processes according to the present invention may be illustrated by the following:

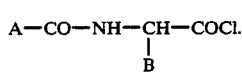

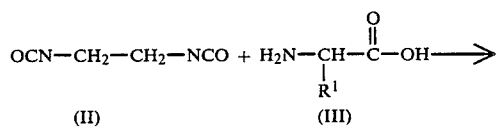

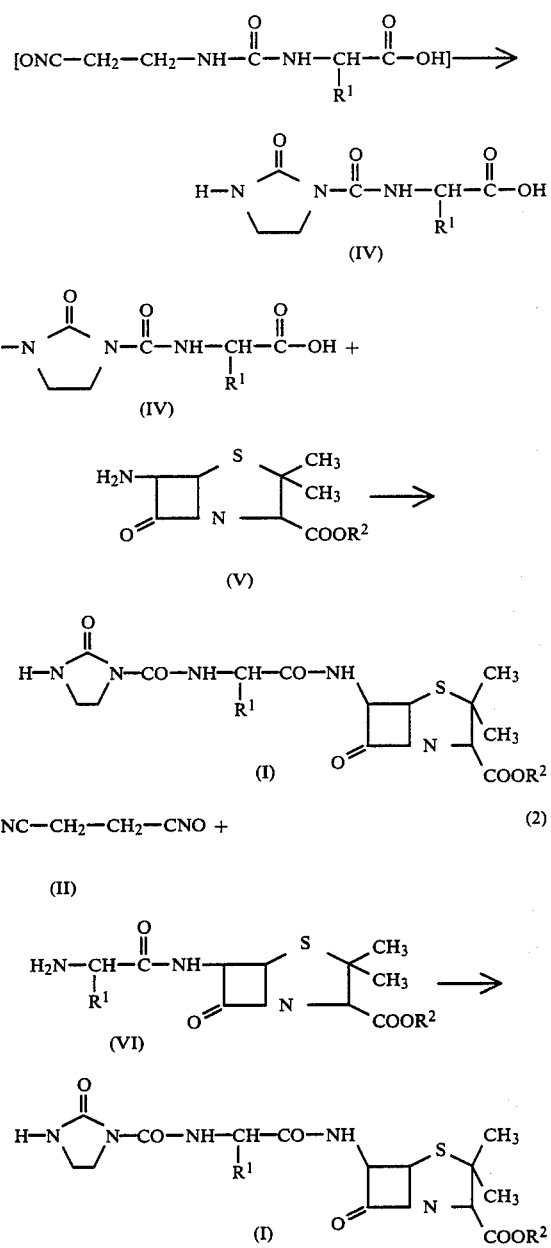

wherein
R¹ and R² are the same as defined before; and
ethylene diisocyanate of formula (II) may be prepared by known methods.

The present invention provides one process that the object compounds of formula (I) can be prepared by reacting ethylenediisocyanate of formula (II) with amino acid of formula (III) to obtain acylureido derivatives of formula (IV), and then acylureido derivatives of formula (IV) with 6-amino penicillanic acid or its salt of formula (V). Ethylene diisocyanate of formula (II) and amino acid of formula (III) are preferably employed in stoichiometric amounts. This reaction was conducted in an appropriate organic solvent or its aqueous solution such as dioxane, tetrahydrofuran, acetone, acetonitrile dimethylsulfoxide or its aqueous solution that is adjusted to an alkaline condition of pH from 7.0 to 10.0 with triethyleneamine or sodium hydroxide under reaction temperature of from −10° C. to reflux temperature. Reaction times are preferably from 1 hour to 7 hours.

The reaction of acylureido derivatives of formula (IV) and 6-amino penicillanic acid or its salt of formula (V) can be carried out with a known process. The present invention also provides another process in which the object compounds of formula (I) may be prepared by reacting ethylendiisocyanate of formula (II) with penicillin derivatives of formula (VI). Ethylenediisocyanate of formula (II) and penicillin derivatives of formula (VI) are preferably employed in stoichiometric amounts and this reaction was conducted in an appropriate organic solvent or its aqueous solution such as dimethylsulfoxide, doxane, tetrahydrofuran or its aqueous solution that was adjusted pH from 7.5 to 10.0 with triethylene amine or sodium hydroxide. Reaction temperature was from −10° C. to reflux temperature, more preferably from 5° C. to room temperature and reaction time was from 30 minutes to 8 hours, more preferably from 1 hour to 3 hours.

As a result, the present invention provides a particularly easy and economical process for preparation of acylureido penicillin derivatives starting from ethylenediisocyanate. The following examples are intended to illustrate but not limit the scope of the present invention.

EXAMPLE 1

8.7 g of D-(−)-α-aminobenzyl penicillin was suspended to 90 ml of tetrahydrofuran containing 20% water, and this mixture make to solution by dropping triethyamine with stirring. To this solution maintaining 5° C. with cooling was added 2N-hydrochloric acid aqueous solution to adjust pH of solution from 7.5 to 8.2. Then 2.8 g of ethylenediisocyante was added to the above reaction mixture by dropwise through 30 minutes. The whole mixture was stirred for 1 hour at this temperature. After a natural increase of temperature to room temperature, the reaction mixture was stirred for another 30 minutes at room temperature. 50 ml of distilled water were then added to reaction mixture. After removing all tetrahydrofuran in the mixture by distillation under reduced pressure at room temperature, 50 ml of ethylacetate were added and the pH of the whole mixture was controlled to 1.5 with hydrochloric acid.

The reaction mixture was stirred for 30 minutes at this temperature. Crystalized products were filtered out and washed with ethylacetate, then dried at 40° C. under reduced pressure to yield 10.8 g of D-(−)-α-(imidazolidin-2-one-1-yl-carbonylamino)-benzyl penicillin.

IR(KBr): 3380, 3230, 1784, 1782, 1687, 1639, 1520, 1375, 1219, 735 cm$^{-1}$.

EXAMPLE 2

30 g of D-(−)-α-phenylglycin was suspended to 50 ml of dimethylformamide containing 30% water and dissolved by dropping the 2N-sodium hydroxide solution with stirring. After cooling this solution to 5° C., the pH of the reaction mixture was adjusted to 7.6 with 2N-hydrochloric acid solution. 2.3 g of ethylenediisocyanate were added to the mixture by dropwise through 20 minutes. The whole mixture was stirred at this temperature for 1 hour. It was left to stand until the temperature of the reaction mixture increased naturally to room temperature, upon which the mixture was stirred at room temperature for 30 minutes.

After 30 ml of distilled water were added to the reaction mixture, all dimethylformamide was distilled under reduced pressure and temperature below 50° C. Any insoluble mixture was filtered out and filtrate was cooled to 5° C., then 4.5 ml of ethylacetate were added to filtrate. Reaction mixture was adjusted pH to 1.5 with 2N-hydrochloric acid and was stirred at this temperature for 30 minutes. After layers were separated an organic layer was dried with magnesium sulfate, the reaction mixture was distilled under reduced pressure to yield 3.9 g of D-(−)-α-(imidazolidin-2-one-1-yl)-carbonyl amino-phenylacetic acid.

IR(DMSO): 1720, 1670, 1525, 1480 cm$^{-1}$.

EXAMPLE 3

Following the same procedure of example 1, but employing D-(−)-α-amino-(P-hydroxy)-benzyl penicillin and ethylenediisocyanate as starting material, D-(−)-α-(imidazolidin-2-one-1-yl-carbonyl amino)-(p-hydroxy)-benzyl penicillin was prepared with similar yield.

EXAMPLE 4

Following the same procedure of example 2, but employing D-(−)-α-(p-hydroxy)-phenylglycin and ethylene diisocyanate as starting material, D-(−)-α-[(imidazolidin-2-one-1-yl)-carbonyl amino]-(p-hydroxy)-phenylacetic acid was prepared.

What is claimed is:

1. A process for preparing acylureido penicillin derivatives having the formula:

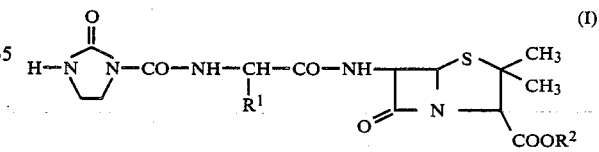

wherein
R$^1$ is phenyl or hydroxyphenyl;
R$^2$ is a member selected from the group consisting of hydrogen, a protecting group, sodium, potassium and calcium,
characterized by reacting ethylenediisocyanate of the formula:

with penicillin derivatives of the formula:

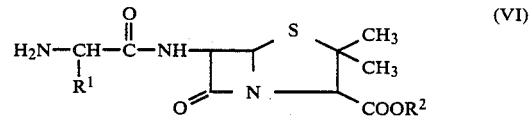

wherein
R$^1$ and R$^2$ are the same as defined above, in a suitable organic solvent or its aqueous solution under alkaline condition a reaction temperature from −10° C. to reflux temperature.

2. A process according to claim 1 characterized by reacting ethylenediisocyanate of the formula:

with amino acid of the formula:

$$NH_2-\underset{R^1}{CH}-\overset{O}{\overset{\|}{C}}-OH \qquad (III)$$

wherein $R^1$ is phenyl or hydroxyphenyl; in suitable organic solvent or its aqueous solution under alkaline condition at reaction temperature from 0° C. to room temperature to obtain acylureido derivatives of the formula:

$$\text{(IV)}$$

(structure IV: imidazolidinone ring with H-N and N-CO-NH-CH($R^1$)-CO-O-H)

wherein $R^1$ is the same as defined above, thereafter reacting acylureido derivatives with 6-amino penicillin or its salt of the formula;

$$\text{(V)}$$

(structure V: 6-aminopenicillanic acid with $H_2N$, S, $CH_3$, $CH_3$, N, $COOR^2$)

wherein $R^2$ is a member selected from the group consisting of hydrogen, a protecting group, sodium, potassium and calcium.

* * * * *